United States Patent [19]

Claypool

[11] Patent Number: 4,488,648
[45] Date of Patent: Dec. 18, 1984

[54] FLAW DETECTOR

[75] Inventor: Mark P. Claypool, Horseheads, N.Y.

[73] Assignee: Powers Manufacturing, Inc., Elmira, N.Y.

[21] Appl. No.: 375,644

[22] Filed: May 6, 1982

[51] Int. Cl.³ .................. B07C 5/34; G01N 21/90; H04N 7/02
[52] U.S. Cl. ................. 209/526; 250/223 B; 356/240; 356/428; 358/106; 364/507
[58] Field of Search ............. 209/522, 523, 524, 526, 209/546, 548, 549, 551; 250/223 B, 563; 356/240, 428; 358/106; 364/506, 507, 552

[56] References Cited

U.S. PATENT DOCUMENTS

| | | | |
|---|---|---|---|
| 3,770,969 | 11/1973 | Ansevin et al. | 209/526 X |
| 3,777,169 | 12/1973 | Walter et al. | 358/106 X |
| 3,880,750 | 4/1975 | Butler et al. | 209/526 |
| 3,886,356 | 5/1975 | Gomm et al. | 250/223 B |
| 3,887,284 | 6/1975 | Gender et al. | 209/526 X |
| 3,900,265 | 8/1975 | Merlen et al. | |
| 3,997,780 | 12/1976 | Waehner | |
| 4,002,823 | 1/1977 | Van Oosterhout | 358/106 |
| 4,026,414 | 5/1977 | Ellinger | 209/524 |
| 4,136,930 | 1/1979 | Gomm et al. | 358/106 |
| 4,292,672 | 9/1981 | Southgate | 364/507 |
| 4,364,113 | 12/1982 | Sengebusch et al. | 364/507 |
| 4,376,951 | 3/1983 | Miyazawa | 358/106 |
| 4,378,494 | 3/1983 | Miller | 209/526 X |
| 4,390,782 | 6/1983 | Vornfett | 209/524 X |

FOREIGN PATENT DOCUMENTS

| | | |
|---|---|---|
| 37694 | 10/1981 | European Pat. Off. |
| 1508035 | 4/1978 | United Kingdom |
| 1530723 | 11/1978 | United Kingdom |
| 1585919 | 3/1981 | United Kingdom |
| 1600400 | 10/1981 | United Kingdom |
| 2078948 | 1/1982 | United Kingdom |
| 2080946 | 2/1982 | United Kingdom |
| 2089973 | 6/1982 | United Kingdom |
| 2089977 | 6/1982 | United Kingdom |
| 2096763 | 10/1982 | United Kingdom |
| 2036301 | 3/1983 | United Kingdom |
| 2104651 | 3/1983 | United Kingdom |

Primary Examiner—David A. Scherbel
Assistant Examiner—Edward M. Wacyra
Attorney, Agent, or Firm—Seidel, Gonda & Goldhammer

[57] ABSTRACT

Container flaws are detected by repetitively sampling the output of a photosensor at a controlled rate dependent on the speed of inspection. Samples are digitized and stored in memory on a first in, first out basis. First in (oldest) and last in (newest) samples are used to provide a sliding computation of the slope or rate of change of the photosensor output. The computed slope is compared to an empirically determined preselected number. Containers are rejected or accepted based on the results of the comparison.

32 Claims, 10 Drawing Figures

SAMPLE & HOLD INPUT

FIG. 3B

A/D CONVERTER INPUT

FLAW DETECTOR

BACKGROUND OF THE INVENTION

The present invention is directed to a flaw detector and to a method of flaw detection. In particular, the invention is directed to a sliding slope technique for detecting container flaws. Such flaws include checks, cracks, chips and line overs which are often found in containers such as glass bottles. A check is a split in the glass bottle which arises from uneven cooling. A crack is a split due to mechanical forces. A chip is a missing or crumbled piece of glass. A line over is a groove in the top surface or finish of the bottle.

Typically, flaw detection is performed as the container is rotated. An optical system including a light source and photosensor scans a portion of the container surface. The level of the photosensor output is proportional to the changing light transmitted through or reflected from the surface. A flaw such as a check or crack directs increased or brilliant light to the photosensor. The increased light is sensed as a "light spot". A flaw such as a chip or line over attenuates the light incident on the photosensor. The attenuated light is sensed as a "dark spot". Signal processing circuitry is usually employed to amplify and shape the photosensor output in preparation for comparison to a predetermined threshold level ("amplitude comparison" technique). If the amplitude of the processed signal (or an average amplitude) exceeds the amplitude of the threshold level, the container is regarded as a reject. A rejected container is ejected from the line.

Using an amplitude comparison technique to detect flaws poses difficult problems. Changes in light incident on the photosensor due to normal container surface characteristics, such as threads, seams, seeds, neck rings and blisters, interfere with and even resemble changes arising from flaws such as checks and cracks. Distinguishing between such normal surface characteristics and true flaws is troublesome.

One solution is to mask the field of view of the photosensor. By this technique, the field of view is limited to a relatively small section of the container surface void of threads, seams or other such problem areas. Masking the photosensor, however, complicates set-up and is often unduly time consuming. Additionally, since photosensor masking drastically reduces the field of view of the photosensor, it is necessary to provide additional sensors to fully examine the container.

Detection of flaws such as chips on the inside finish of a glass bottle and line overs cutting across the top finish have been especially difficult to detect. As mentioned previously, these flaws are sensed as "dark spots" in the bottle finish and may be indistinguishable from ambient light.

Conventional optical inspection systems are described in U.S. Pat. Nos. 4,002,823 (Van Oosterhout) issued Jan. 11, 1977 and 4,136,930 (Gomm et al.) issued Jan. 30, 1979. U.S. Pat. No. 4,002,823 discloses a system for detecting defects in articles such as glassware. A video camera receives semi-diffused light passing through the glassware. The video signal is representative of the spatial rate of change of the refraction characteristics of the glassware. The signal is filtered and peak-detected to discriminate between normal marks and defects. An instantaneous amplitude value is taken and compared to a running average ("average amplitude comparison" technique). A defect pulse is generated when the instantaneous amplitude exceeds the running average.

U.S. Pat. No. 4,136,930 discloses a system for detecting foreign particles in the liquid contents of a bottle. The bottle is first viewed by a video camera which "memorizes" its optical characteristics. The bottle contents are then agitated to cause any foreign particles to shift position. The bottle is then viewed by a second camera. Movement of the foreign material changes the optical characteristics viewed by the camera. Differences in amplitude between adjacent video pulses indicate the presence of foreign material.

Other optical inspection schemes are disclosed in U.S. Pat. Nos. 3,886,356, 3,900,265 or 3,997,780.

U.S. Pat. No. 3,886,356 discloses an optical scanner for identifying defects in a transparent item by measuring the light transmitting qualities of the item. Circuitry responsive to change in signal amplitude is employed to detect the presence of defects.

U.S. Pat. No. 3,900,265 discloses a laser scanner for flaw detection. The scanner responds to changes in the amplitude of light reflected from the surface being inspected.

U.S. Pat. No. 3,997,780 discloses a label orientation inspection system. A vidicon camera views a pattern generated by an array of fiber optic cables focused on a bottle. The pattern is compared with a reference pattern to determine proper alignment of the label.

SUMMARY OF THE INVENTION

A container surface is optically scanned for flaws which produce "light spots" or "dark spots", without photosensor masking, facilitating rapid set-up. Flaws are accurately detected using a sliding slope computation. The sliding slope computation is based on the repetitive sampling of the photosensor output signal which is indicative of the optical characteristics of the container surface. A predetermined number of samples of the signal are successively stored in memory and updated on a first in, first out basis. The slope computation is performed between successive updates of the stored samples. The difference between two of the stored samples, preferably the oldest and newest samples, is computed, and the computed difference is compared to a preselected number. Based on the comparison, a signal is generated to indicate whether the container should be rejected. Running counts are made of the total number of containers inspected and the total number rejected.

A flaw, such as a check, generally produces a much faster fluctuation in light incident on the photosensor than that produced by normal surface anomalies such as threads, seams, seeds, neck rings and blisters. By examining the slope of the photosensor signal, rather than its absolute amplitude, flaws are accurately and reliably detected while anomalies not detrimental to the end use of the container are accepted. Moreover, accurate and reliable detection of flaws is ensured by the sliding slope technique even though the amplitude of the fluctuation of light incident on the photosensor due to the flaw may be the same as or even less than the amplitude of fluctuation of incident light due to a harmless anomaly. As a result, a larger surface area of the container can be optically scanned without masking the photosensor.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
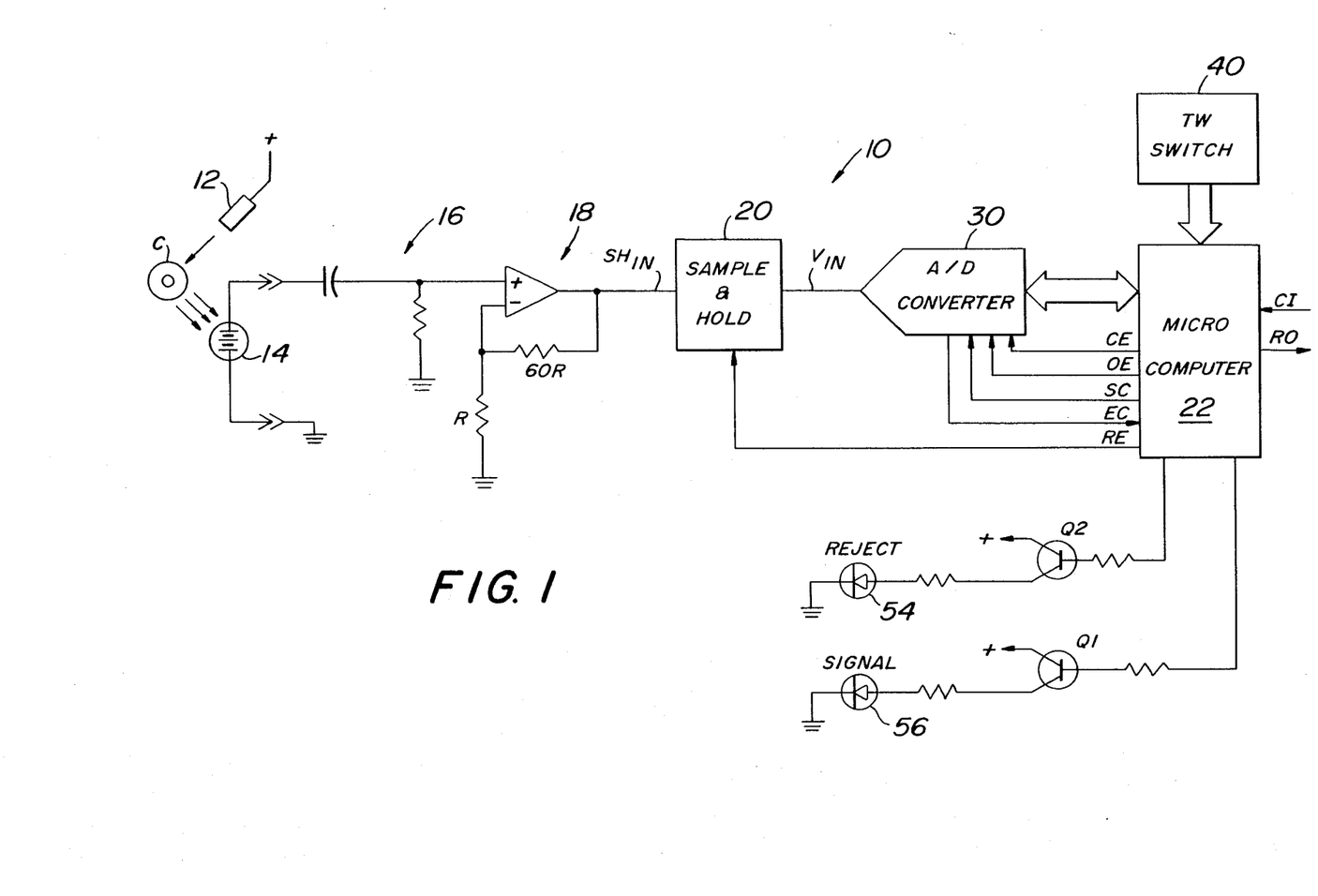
FIG. 1 is a block diagram of the flow detector of the present invention utilizing a non-inverting amplifier for detection of flaws which produce "light spots".

Referring to the drawings in detail, wherein like numerals indicate like elements, there is shown in FIG. 1 a block diagram of the flaw detector of the present invention designated generally as 10. One or more light sources 12 and photosensors 14 (only one pair being shown for simplicity) are focused on selected locations along the container surface. Different numbers and arrangements of light sources and photosensors may be employed as is well known in the art. Preferably, several flaw detectors may be employed, one for each photosensor.

Light source 12 is preferably a dc light source. Light is directed from the light source to the container C. Incident light is directed by a flaw, such as a crack or chip, in the surface of the container C by reflection or transmission to the photosensor 14.

The output of the photosensor 14 is capacitively coupled through an RC circuit 16 to an amplifier 18. As shown in FIG. 1, the amplifier 18 comprises a non-inverting operational amplifier such as a TL082 having a gain of approximately 60:1. The amplifier 18 is used to detect "light spots", that is, a pulse of enhanced or brilliant light directed from a flaw in container C to the photosensor 14. To detect "dark spots", that is, a relatively sharp decrease in the light impinging on photosensor 14 due to a flaw in container C, an amplifier 18' is used (FIG. 6) instead of amplifier 18. Both amplifiers may be provided on a single printed circuit board, and they may be used alternatively by means of jumper or switch connections. Detection of "dark spots" and further details as to the nature of amplifier 18' are provided in a later section of the specification.

Figure 3A:
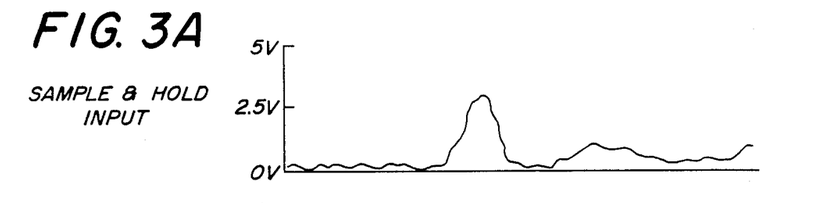
FIGS. 3A and 3B are diagrams of representative signals appearing at the sample and hold circuit input and output.

The output (SHin) of amplifier 18 is connected to a sample and hold circuit 20 which is supervised by a programmed microcomputer 22. A representative pulse output of amplifier 18 is shown in FIG. 3A for the case of a sharp increase in light incident on photosensor 14 ("light spot").

Figure 2:
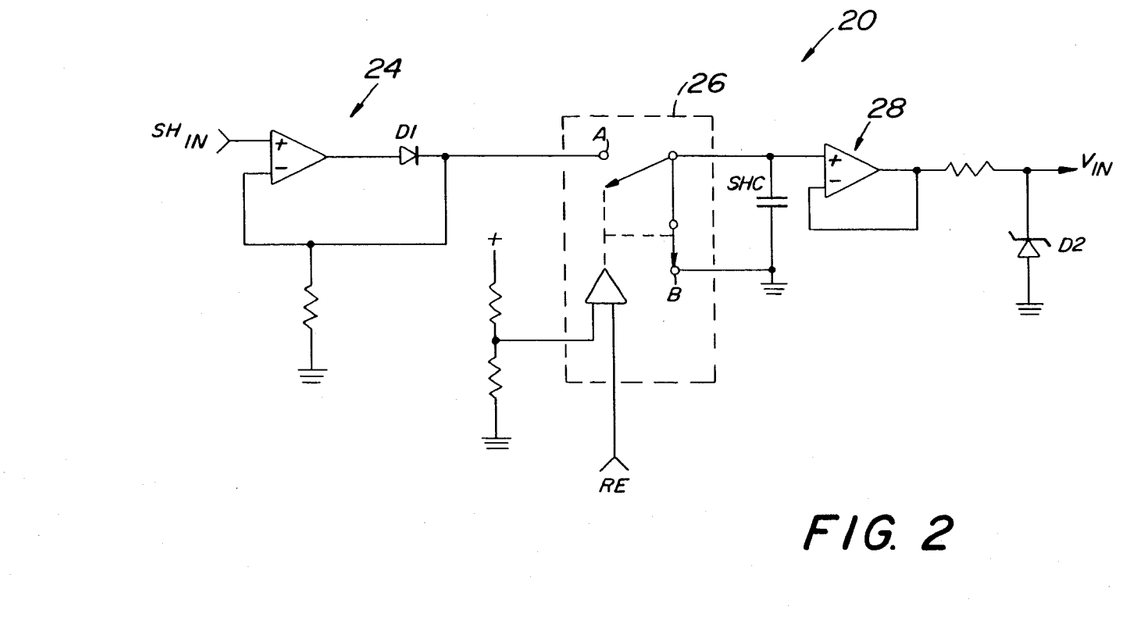
FIG. 2 is a schematic of the sample and hold circuit.

Preferably, the sample and hold circuit 20 is a buffered sample and hold/peak detection circuit as shown in detail in FIG. 2. The sample and hold circuit 20 includes a peak detector 24 for detecting the rising and falling edges of the SHin pulse signal. The peak detector 24 is a well-known circuit configuration which includes a non-inverting operational amplifier of the TL082 type connected to a diode D1.

The peak detector output is connected to an analog switch 26 of the AH0142 type. The analog switch 26 is shown in the reset state in FIG. 2 with switch S1 removed from terminal A and switch S2 connected to terminal B. For this condition, the sample and hold capacitor SHC discharges to ground.

The peak detected signal at terminal A is sampled and held when the analog switch 26 is in the enable state. In the enable state, the switch S1 is connected to terminal A and switch S2 is disconnected from terminal B.

Control of the analog switch 26 between the reset and enable states is maintained by a reset/enable (RE) signal produced by the microcomputer 22. The RE signal repetitively transfers the analog switch 26 between the reset and enable states to provide successive samples of the peak detected signal at terminal A to an analog to digital converter 30.

Figure 3B:
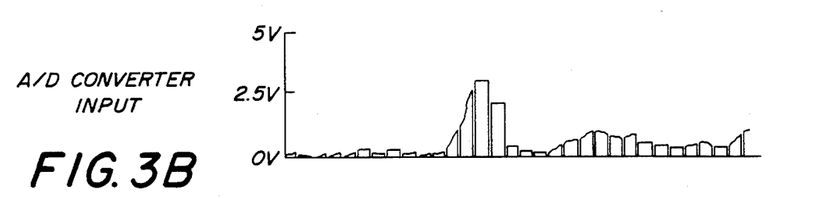

The sample and hold capacitor SHC is buffered by a unity gain amplifier 28 comprises a TL082 operational amplifier connected in the non-inverting mode. A representative amplifier 28 output, designated Vin, is shown in FIG. 3B. This output comprises successive samples of the amplified photosensor signal.

The sample and hold circuit 20 is connected to analog to digital converter 30. Analog to digital converter 30 is an ADC0804 analog to digital converter. The input to the analog to digital converter 30 is the unity gain amplifier output Vin shown in FIG. 3B. Successive samples at the Vin output of amplifier 28 are converted to 8 bit digital words by the analog to digital converter.

The data output of the analog to digital converter is coupled by an 8 bit tri-state data bus to the microcomputer 22. Conversion of the samples of the photosensor signal by analog by digital converter 30 is controlled by the chip enable (CE) and start conversion (SC) signals generated by the microcomputer. The end of a sample conversion is indicated by an end of conversion (EC) signal generated by the analog to digital converter. Operation of the analog to digital conversion in response to these signals is described more fully hereafter in connection with the waveforms shown in FIG. 4.

Speed Compensation

Preferably, the sample and hold circuit 20 and analog to digital converter 30 are operated at a rate determined by the microcomputer 22 based on the speed at which the container is moved through the inspection station. The speed at which the container is moved through the inspection station determines the duration of the inspection interval, i.e., the time available for inspecting the container for flaws. As the machine speed increases, less time is available for inspecting the container. Accordingly, unless the sampling rate is increased too few samples will be taken of the photosensor signal and system resolution will suffer. Thus, despite the reduction in duration of the inspection interval, it is desirable to obtain at least a certain minimum number of samples to maintain system resolution. The effective sampling rate, or the rate at which samples are provided to the microcomputer, is therefore automatically varied to ensure that the proper number of samples is obtained as machine speed varies.

EXAMPLE

Typically, a procession of containers is conveyed through the inspection station in line on a driven conveyor. An adjustable speed rotator belt (not shown) located at the inspection station contacts and rotates each container about its longitudinal axis. As the container is rotated, it may be temporarily stopped or shunted off the conveyor or it may continue to move on the conveyor through the station. If the container is stopped while it is being rotated, the light source 12 and photosensor 14 may be mounted in a stationary manner at the station. Preferably, the container continues to move on the conveyor through the inspection station as the container is rotated, and the light source 12 and photosensor 14 are mounted on a carriage which moves in synchronism with the conveyor as is well known in the art.

In either case, it is desirable to rotate the container somewhat more than 360° during an inspection interval to ensure that the entire surface of the container is inspected. Preferably, the container is rotated 1¼ revolutions or 405° for this purpose. As the machine speed increases, the container is rotated more rapidly through the full 405° rotation at the inspection station. The microcomputer 22 automatically varies the rate of operation of the sample and hold circuit 20 and analog to digital converter 30 to ensure that the desired number of samples is obtained for any inspection interval and machine speed.

For example, assume a maximum machine speed of 240 containers per minute passing through the inspection station. Typically, an inspection interval is confined to one-third of the time that the container takes to pass through the inspection station. In this case, the time required for the container to pass through the inspection station is 0.250 seconds. The shortest expected inspection interval is therefore 0.0833 seconds long.

There is a maximum rate at which samples can be supplied by the sample and hold circuit 20 and the analog to digital converter 30 to the microcomputer. This rate is essentially fixed by the time required for the analog to digital converter to effect a conversion. The microcomputer is programmed to operate the sample and hold circuit 20 in tandem with the analog to digital converter 30 so that samples are supplied to the microcomputer at the maximum rate when the machine is operating at maximum speed. For the analog to digital converter described, the maximum rate at which samples can be supplied to the microcomputer is approximately 200 microseconds per sample. Accordingly, approximately 416 samples are obtained and transferred in digital form to the microcomputer during 0.0833 seconds, the shortest expected inspection interval.

As the machine speed decreases, the microcomputer 22 operates the sample and hold circuit 20 and analog to digital converter 30 at lower rates to ensure that approximately 416 samples are transferred to the microcomputer 22 for 405° rotation of the container during any inspection interval.

Under the foregoing assumptions, if the machine speed is decreased to provide 150 containers per minute through the inspection station, then the inspection interval is approximately 0.1333 seconds long. To ensure that 416 samples are obtained during the inspection interval, the sample and hold circuit 20 and analog to digital converter 30 must be operated by the microcomputer to provide a sample at the analog to digital converter data outputs every 320 microseconds.

If the machine speed is decreased further to provide 60 containers per minute through the inspection station, the slowest machine speed, the inspection interval increases to approximately 0.333 seconds. Accordingly, to provide 416 samples to the microcomputer during the inspection interval, the microcomputer operates the sample and hold circuit 20 and analog to digital converter 30 at the reduced rate of 801 microseconds per sample.

In all examples provided above, 416 samples are provided to the microcomputer per 405° rotation of the container. In other words, a sample is provided at the analog to digital converter output at least every 1° of rotation of the container. This assures that the computer is provided with uniform information at all machine speeds.

Changing the Sampling Rate

Figure 4:
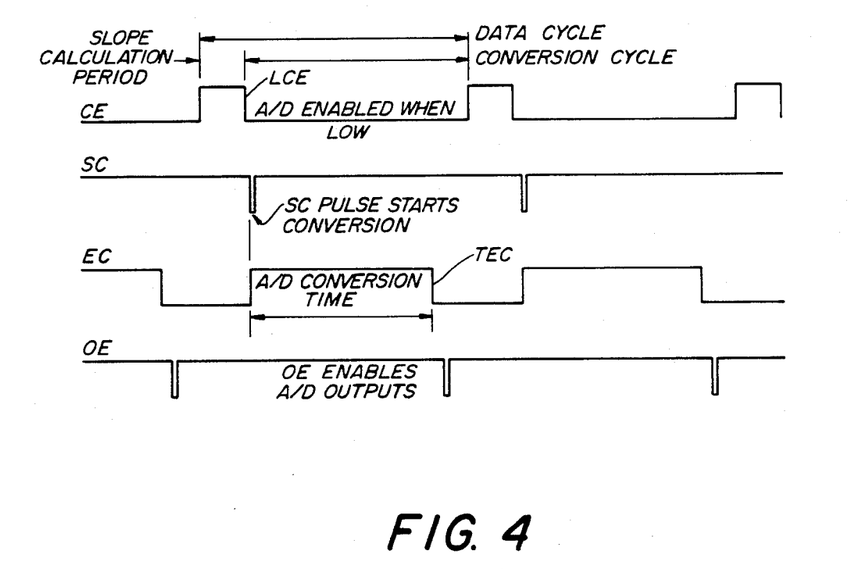
FIG. 4 is a timing diagram of a data cycle showing synchronous operation of the sample and hold circuit and the analog to digital converter.

Varying the rate of operation of the analog to digital converter 30 under supervision of programmed microcomputer 22 is best shown shown by timing diagrams in FIG. 4.

Referring to FIG. 4, the time required for the microcomputer to effect a slope calculation (described more fully below) and to obtain and transmit a new sample to the microcomputer in preparation for the next slope calculation is denoted as the "data cycle". There are approximately 416 such data cycles for the examples given above, one for each sample. During each data cycle, the analog to digital converter converts the analog sample provided by sample and hold circuit 20 to digital form. The time required for the analog to digital converter to convert a sample to digital form within the data cycle is fixed and is denoted in FIG. 4 as the "conversion time". The sample and hold circuit 20 is reset by the RE signal between successive data cycles.

The chip enable (CE) signal disables the analog to digital converter during a slope calculation by the microcomputer. Once the slope calculation is performed, the leading edge LCE of the CE pulse (negative going) enables the analog to digital converter, and the start conversion (SC) pulse (negative going) initiates a conversion of the newest sample to digital form a fixed time thereafter.

Conversion of the sample to digital form takes place during an end of conversion (EC) pulse (positive going). The trailing edge TEC of the EC pulse indicates that the conversion is completed. The microcomputer detects the trailing edge of the EC pulse and generates the output enable (OE) signal (negative going pulse) a fixed time thereafter. The OE signal conditions the converter outputs to transmit the newest digital sample to the microcomputer over the tri-state data bus. The microcomputer utilizes the newest digital sample to effect a slope calculation in the immediately ensuing data cycle.

By changing the time at which the leading edge of the CE signal occurs as machine speed varies, the microcomputer varies the effective sampling rate and guarantees that the desired number of samples is obtained for any size inspection interval.

Detecting Changes in Machine Speed

Figure 5:
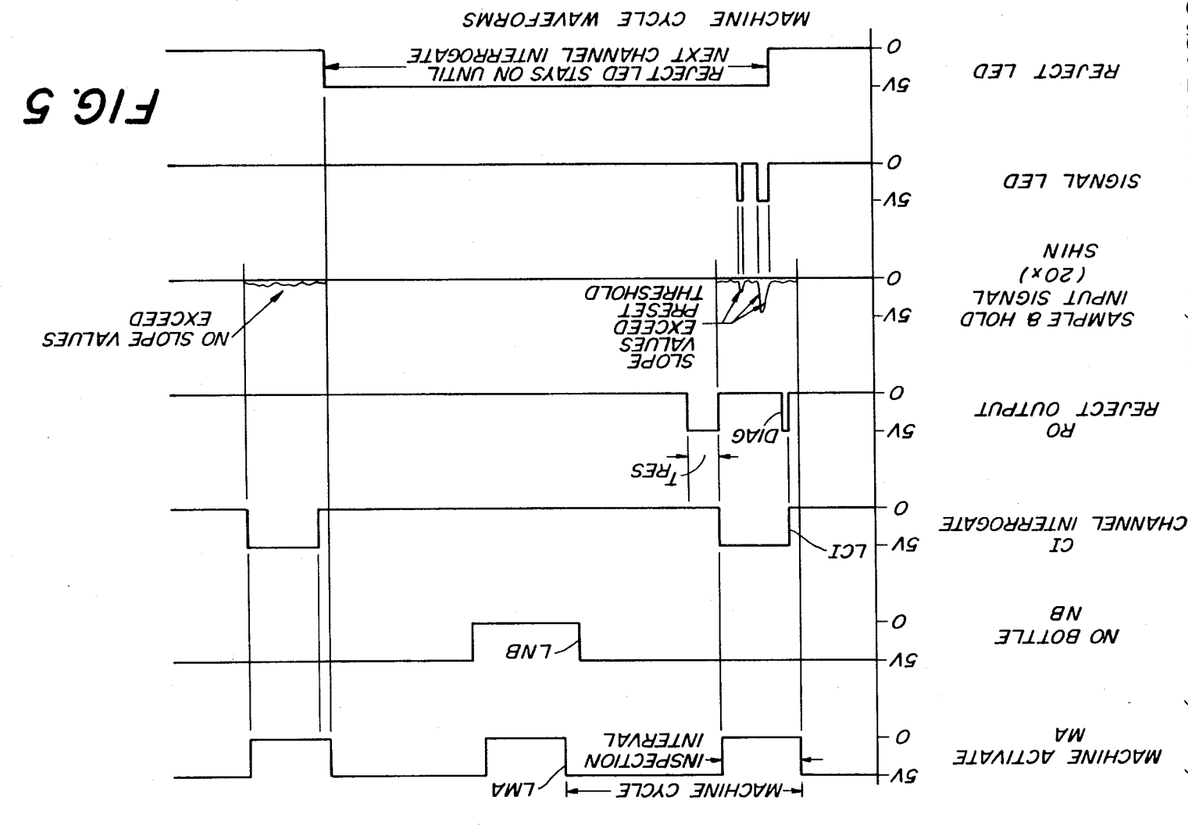
FIG. 5 is a timing diagram showing successive operation of the invention for several inspection intervals and conditions.
Figure 9:
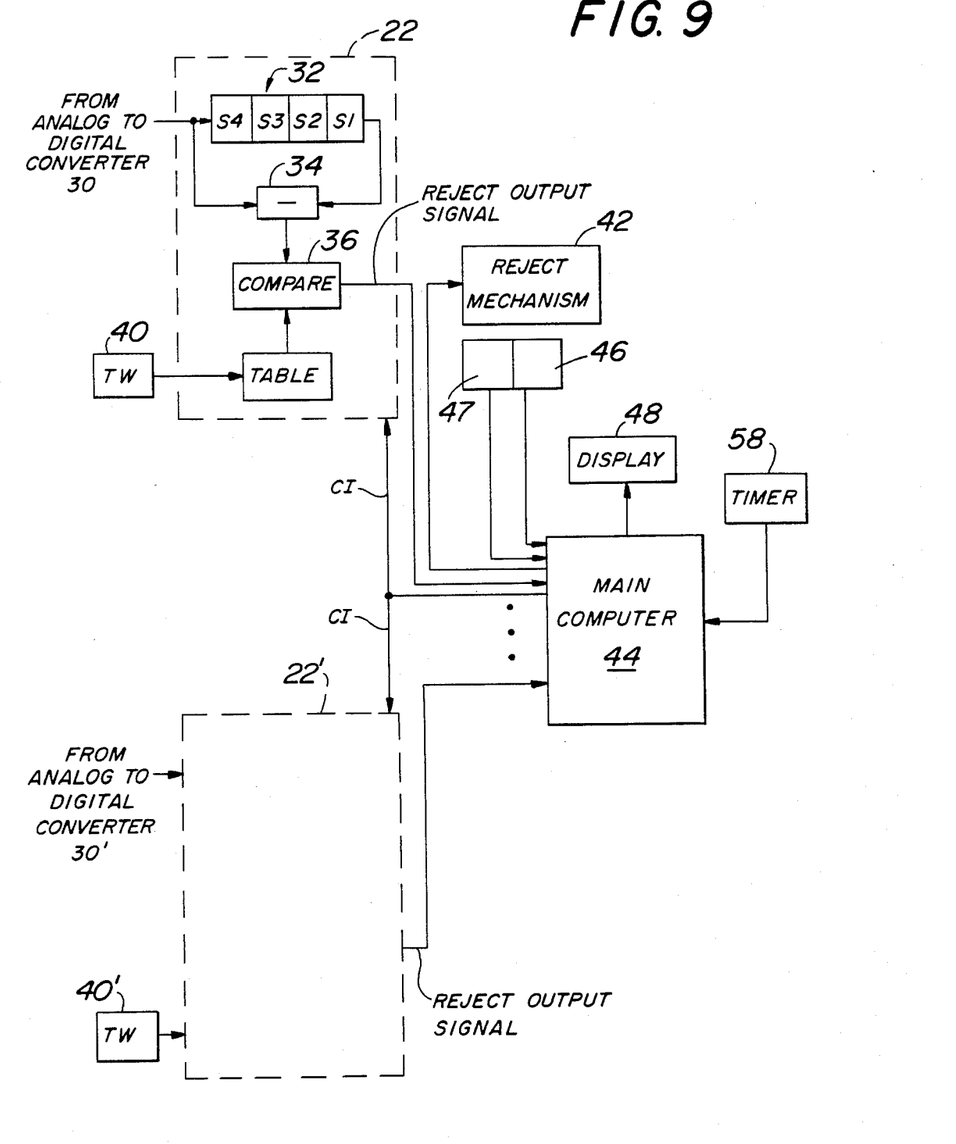
FIG. 9 is a functional block diagram showing operation of identically programmed microcomputers for each of several flaw detectors operated in tandem with a main computer and display.

The microcomputer maintains a count of timing pulses during each inspection interval. The start and finish of an inspection interval is signaled by a cam activated switch 46 (FIG. 9). Operation of switch 46 is well known in the art. The switch 46 is operated in synchronism with the conveyor drive (not shown) and generates a machine activate (MA) pulse (negative going) as shown in FIG. 5 during a machine cycle. The duration of the MA pulse essentially represents the duration of the inspection interval. Accordingly, any increase in machine speed, i.e., the speed at which containers are conveyed through the inspection station, will result in more rapid actuation of switch 46 and a shorter MA pulse. For a machine speed of 240 containers per minute, the MA pulse is approximately 0.0833 seconds long as previously indicated.

As explained more fully below in connection with FIG. 5, the MA pulse is detected by main computer 44. Once the MA pulse is detected, the main computer generates a channel interrogate (CI) pulse (positive going). The CI pulse initiates a data cycle. The CI pulse is generated a short (fixed) time after the leading edge of the MA pulse for purposes of diagnostic testing. The trailing edges of the MA and CI pulses coincide. During the CI pulse, the microcomputer counts high frequency pulses generated for example every 70 microseconds by an internal microcomputer oscillator (not shown). The count of internal oscillator pulses at the end of the CI pulse is therefore indicative of machine speed. At the end of the CI pulse, the count is stored for use in the next inspection interval.

Any change in machine speed is reflected as a change in the internal oscillator count at the end of the CI pulse. Based on the change, the microcomputer automatically alters the time at which the leading edge LCE of the CE pulse occurs. As machine speed increases, the leading edge of the CE signal occurs earlier thereby increasing the data cycle frequency. As machine speed decreases, the leading edge of the CE signal occurs later, thereby reducing the data cycle frequency. Until the leading edge of the CE pulse occurs, the analog to digital converter remains disabled, the start conversion (SC) pulse cannot be generated, and no further sample can be converted and transmitted to the microcomputer. In this manner, the effective sampling rate, i.e., the rate at which photosensor samples are fed to the microcomputer, is varied as a function of machine speed.

Slope Calculation

Referring to FIG. 9, there is shown a functional block diagram of the operations performed by the microcomputer 22. Digital samples are transmitted during successive data cycles from the analog to digital converter 30 to the microcomputer where the samples are temporarily stored in a memory 32. Preferably, the memory 32 stores four successive samples transmitted from the analog to digital converter. The samples are designated S1–S4 in FIG. 9. Each sample is an 8 bit word transmitted over the data bus connecting the analog to digital converter and the microcomputer. As a new sample is stored in memory 32, the oldest stored sample S1 is transferred out of memory to a difference logic unit 34. Each sample, then, is stored in memory for four data cycles, used to compute slope for two data cycles, and is then disposed of. It should be appreciated that the storage and retrieval scheme shown conceptually in FIG. 9 is the well known first in, first out (FIFO) scheme. Preferably, the microcomputer 22 is programmed to store and retrieve the analog to digital converter samples on a FIFO basis using a memory pointer. Thus, samples are not actually shifted through hardware to obtain the desire storage and retrieval pattern.

The difference logic unit 34 utilizes well known arithmetic logic operations to derive the difference between the oldest sample S1 and the newest sample S4 stored in memory 32 during any data cycle. The computed difference is representative of the slope of the photosensor output and is compared by comparison logic 36 to a slope threshold level in the form of a preselected number stored in a memory table 38. The memory table 38 may for example hold 15 such numbers representative of 15 slope thresholds.

The microcomputer 22 is programmed to select a particular number from the memory table 38 for comparison to the computed slope based on the setting of a sensitivity thumbwheel switch 40. In effect, the setting of the thumbwheel switch 40 serves as an address for the memory table 38. Each of the numbers stored in memory table 38 is empirically derived based on a random sampling of containers having assorted types of flaws. The numbers may vary from application to application, depending on the type of container being inspected and the type of flaws expected.

The foregoing computations are repeated during successive data cycles to provide a "sliding" slope calculation, i.e., successive slope calculations, throughout the inspection interval. For the present example, any size inspection interval includes approximately 416 data cycles. If, during any data cycle the difference computed by difference logic unit 34 exceeds the preselected number retrieved from table 38, the comparison logic unit 36 generates a Reject Output (RO) signal which indicates that the container should be rejected (FIGS. 5 and 9).

Reject Output (RO) Signal

The RO signal may be utilized to activate a reject mechanism 42, such as a paddle, to eject the rejected container from the conveyor line. For this purpose, the RO signal is transmitted to a main computer 44. The main computer triggers the reject mechanism 42 when the RO signal is received. The RO signal is also used to increment an internal counter in main computer 44 to maintain a count of the number of containers that have been rejected.

The main computer 44 also maintains a count of the total number of containers inspected at the inspection station. For this purpose, a contact switch 47 may be provided at the inspection station to detect the presence of a container during an inspection interval, i.e., during an MA pulse. The main computer 44 senses the state of switches 46 and 47 to determine whether to initiate a data cycle as described in greater detail hereinafter. If switch 47 indicates presence of a container, the main computer transmits a channel interrogate (CI) pulse to the microcomputer and increments an internal counter which indicates the number of containers that have entered the inspection station.

The main computer 44 is associated with a conventional numerical display 48. The count of the total number of containers inspected and the count of the number of containers rejected by flaw detector 22 is displayed on display 48 under control of the main computer.

The invention has thus far been described in terms of a single flaw detector 22 for simplicity. The main computer 44, however, has the capacity to process information from as many as twelve flaw detectors, each flaw detector corresponding to a photosensor 12 focused on a particular container surface area. Information from each flaw detector such as total number of containers inspected and number of containers rejected is used by main computer 44 to control display 48. Thus, the main computer 44 sums the numbers of containers inspected by each flaw detector to derive the total of all containers inspected. The computer 44 also sums the numbers of containers rejected by each flaw detector to derive the total of all containers rejected. These totals are displayed by display 48 together with the numbers of containers rejected by each flaw detector.

Display of Reject

A Reject LED 54 and a Signal LED 56 are provided for each flaw detector (FIG. 1). The Reject LED provides a sustained signal throughout the inspection interval which indicates that the container is a reject. The Signal LED provides a pulse type signal having a duration determined by the duration of the fluctuation at the photosensor output caused by a flaw.

Operation of the LEDs 54, 56 for one flaw detector during successive inspection intervals and conditions is shown in FIG. 5. In the first inspection interval, the container exhibits two flaws. During a machine cycle, cam activated switch 46 and contact switch 47 are sensed by the main computer 44. The switch 46 generates a negative MA pulse to indicate the inspection interval. The switch 47 generates a negative pulse, denoted NB, only if no container is present at the inspection station. The CI signal is generated by the main computer a short time (fixed) after the start of the MA signal, to afford the main computer an opportunity to inspect the RO signal line during a diagnostic test described hereafter. The CI pulse is received simultaneously by all flaw detectors. If the NB signal indicates the presence of a container, the main computer 44 sends the CI pulse to the microcomputer 22. This initiates the data cycles previously described in connection with FIG. 4.

In the example shown in FIG. 5, the SHin input to the sample and hold circuit 20 of a flaw detector fluctuates in response to the container flaws, producing two pulse type signals during the first CI pulse. It is assumed that the rising and falling edges of each SHin pulse produce successive slope values which exceed the selected threshold. As a result, the microcomputer 22 drives the Signal LED 56 "on" via transistor Q1, and the LED stays "on" as long as the computed slope exceeds the selected threshold. When the computed slope falls below the threshold, the microcomputer turns the transistor Q1 "off", extinguishing the Signal LED.

When a reject is first detected, as indicated by the Signal LED being driven "on", the Reject LED is also driven "on" by the microcomputer via transistor Q2. The Reject LED is maintained "on", although the Signal LED is eventually turned "off", until the next CI pulse is received from the main computer. Thus, the Reject Output (RO) signal must be generated to eject the container before the Reject LED is extinguished.

At the end of a CI pulse, the microcomputer sends the RO signal to the main computer 44. As shown in FIG. 5, the CI pulse is terminated by the main computer at the end of the MA signal. The CI pulse duration therefore varies directly with MA pulse duration and machine speed.

No Container At Inspection Station

If switch 47 indicates that no container is present at the inspection station during the next inspection interval, by a negative NB pulse as shown in FIG. 5, the main computer 44 does not generate a CI pulse. In particular, the main computer scans the MA and NB signal lines (FIG. 9). If the leading edge LNB of the NB pulse precedes the leading edge LMA of the MA pulse, the main computer does not generate a CI pulse. See FIG. 5. Accordingly, no microcomputer 22 executes a data cycle, no sample is received from any digital to analog converter, and no slope calculation is performed by any flaw detector.

Diagnostic Test

Referring to FIGS. 5 and 9, the main computer 44 generates a CI pulse for all flaw detector microcomputers a short fixed interval following the leading edge LMA of the MA pulse. During this interval, hereafter referred to as the "diagnostic interval", the main computer scans the RO output lines from all microcomputers. Normally, an RO line is "low" during an MA pulse. If an RO line is not "low" during the diagnostic interval, this indicates a malfunction or a defective flaw detector. The computer 44 notes this condition for any such flaw detector by storing the result of the scan in memory.

The main computer then generates the CI pulse to initiate a data cycle for each flaw detector. Each flaw detector microcomputer is programmed to generate a short diagnostic pulse (DIAG) on detecting the leading edge LCI of the CI pulse. The main computer again scans the RO output lines from the microcomputers. If a DIAG pulse does not appear on any RO line, this indicates a microcomputer malfunction. The main computer notes this condition for any such microcomputer by storing the result of the scan in memory.

Following the DIAG pulse, each microcomputer is free to execute a data cycle as previously described. The main computer, however, ignores any signal appearing on the RO line of a flaw detector which produced a "high" level during the diagnostic interval prior to the leading edge LCI of the CI pulse or which failed to produce a DIAG pulse. Additionally, the main computer operates the display 48 to display a warning message, such as HELP, together with a number or other indicia identifying the defective flaw detector.

The main computer 44 also operates display 48 to display a number indicative of machine speed, i.e., the number of containers inspected per minute. For this purpose, an external timer 58 (FIG. 9) is connected to the main computer 44. When the timer times out, the main computer calculates machine speed by dividing the count of total number of containers inspected by the duration of the the timer interval, multiplies the result by a suitable scale factor, and transmits the product in digital form to the display 48. For example, using a 30 second timer, the main computer divides the count of total number of containers inspected by 30 (the timer interval) and doubles the result to derive a figure indicative of machine speed in containers per minute. Of course, timer intervals other than 30 seconds may be used with other scale factors to perform the calculation of machine speed in containers per minute.

Dark Spot Detection

Certain flaws in the container surface, such as chips along the inner finish of the container and line overs cutting across the top finish of the container, appear as "dark spots" to the photosensor. These flaws pose significant problems in detection because the reduction in light incident on the photosensor caused by the flaws is relatively small compared to ambient light. The detection of flaws which produce "light spots", i.e., flaws which produce increases in the light incident on the photosensor, does not pose such a problem because an increase in the amount of light incident on the photosensor is usually relatively large compared to ambient light.

Figure 6:
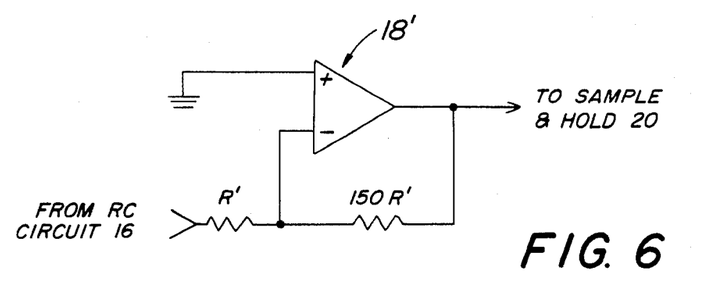
FIG. 6 is a schematic of the high gain inverting amplifier which is substituted for the non-inverting amplifier shown in FIG. 1 to enable detection of flaws which produce "dark spots".

For purposes of "dark spot" detection, the non-inverting amplifier 18 (FIG. 1) is replaced with an inverting amplifier 18' having a relatively high gain (FIG. 6). The amplifier 18' may, for example, have 2.5 (or more) times the gain of amplifier 18. As shown in FIG. 1, the non-inverting amplifier 18 used to detect "light spots" has a gain of 60 R/R=60. The gain of the inverting amplifier 18' in FIG. 5 is 150 R'/R'=150, or 2.5 times the gain of amplifier 18.

A "dark spot" results in a relatively small negative going pulse type signal at the output of RC circuit 16. The inverting amplifier 18' inverts and amplifies the signal. The output of amplifier 18' is then transmitted to the sample and hold circuit 20 and processed as previously described.

Figure 7:
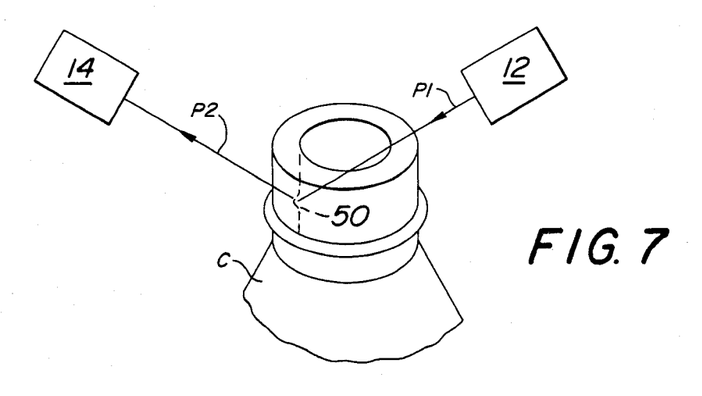
FIG. 7 is a diagram showing an arrangement of the light source and photosensor for detecting chips on the inner finish of a container.

A preferred arrangement of the light source 12 and photosensor 14 for detecting a chip on the inner finish of a container is shown in FIG. 7. The chip 50 tends to reflect light back towards the light source 12, reducing the amount of light incident on the photosensor 14. This results in the detection of a "dark spot" as previously described. Preferably, the light source 12 and photosensor 14 are positioned to be "in-line", that is, the light paths P1 and P2 from the source 12 to the container and from the container to the photosensor 14 lies in a substantially vertical plane intersecting the container C.

Figure 8:
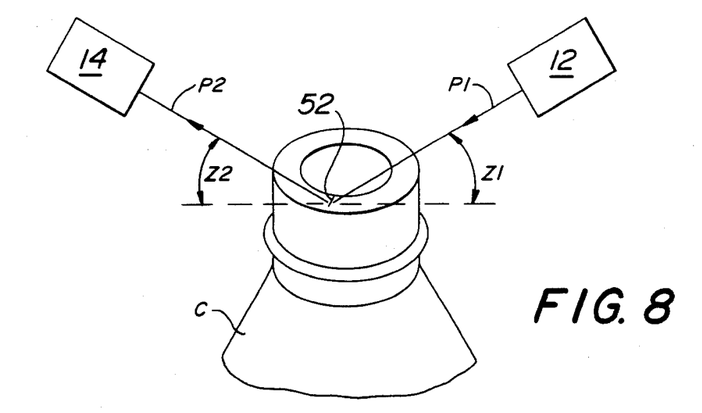
FIG. 8 is a diagram showing an arrangement of the light source and photosensor for detecting line overs on the top finish of a container.

A preferred arrangement for detecting line overs is shown in FIG. 8. The line over 52 produces a reduction in light incident on the photosensor 14 and is detected as a "dark spot" as previously described. The light source 12 and photosensor 14 are aimed at the top finish of the container C such that light paths P1 and P2 describe relatively acute angles Z1 and Z2 respectively with respect to the plane of the top finish (indicated by dashed lines).

The present invention may be described in other specific forms without departing from the spirit or essential attributes thereof and, accordingly, reference should be made to the appended claims, rather than to the foregoing specification, as indicating the scope of the invention.

I claim:

1. Method of inspecting containers for manufacturing defects, comprising:
    optically scanning a portion of the surface of a container during an inspection interval by causing relative angular displacement between the container and an optical scanner,
    generating a signal having a time varying value based on the optical characteristics of the portion of the container surface being scanned,
    processing the signal in real time by repetitively computing the time rate of change of the signal,
    comparing each computed time rate of change to a preselected number, and
    generating a reject signal indicating whether the container should be rejected based on the comparison between the computed time rate of change and the preselected number.

2. Method according to claim 1 including comparing each computed time rate of change to a preselected number at a rate based on the duration of the inspection interval.

3. Method of inspecting containers for manufacturing defects, comprising:
    optically scanning a portion of the surface area of a container during an inspection interval by causing relative angular displacement between the container and an optical scanner,
    generating a signal having a time-varying value based on the optical characteristics of said portion of the container surface being scanned,
    repetitively sampling the signal during the inspection interval,
    storing a predetermined number of samples of the signal,
    updating said stored samples in real time,
    computing the difference between a first updated stored sample and a second updated stored sample,
    comparing the difference to a preselected number, and
    generating a reject signal indicating whether the container should be rejected based on the comparison of the computed difference to the preselected number.

4. Method according to claim 3 wherein said step of repetitively sampling the signal includes repetitively sampling the signal at a sampling and sampling interval rate dependent on the duration of the inspection interval such that the number of samples obtained during any inspection interval is substantially constant.

5. Method of inspecting containers for manufacturing defects, comprising:
    optically scanning a portion of the surface of a container during an inspection interval by causing relative angular displacement between the container and an optical scanner,
    generating a signal having a time varying value based on the optical characteristics of said portion of the container surface being scanned,
    repetitively sampling the signal during the inspection interval at a rate dependent on the duration of the inspection interval such that the number of samples obtained during any inspection interval is substantially constant,
    storing a predetermined number of samples and repetitively updating the stored samples in real time by removing the oldest stored sample and by storing the newest sample,
    computing the difference between the oldest updated stored sample and the newest updated stored sample,
    comparing the computed difference to a preselected number, and
    generating a reject signal indicating whether the container should be rejected based on the comparison of the computed difference to the preselected number.

6. Method according to claims 5 or 4 including determining the duration of a preceding inspection interval, and automatically varying said rate and interval of repetitive sampling of the signal based on the duration of the preceding inspection interval.

7. Method according to claims 1, 3 or 5 including the step of ejecting the container based on said comparison.

8. Method according to claim 7 including generating a diagnostic signal, detecting presence or absence said diagnostic signal, and inhibiting said step of ejecting said container if absence of said diagnostic signal is detected.

9. Method according to claims 1, 3 or 5 including generating a signal indicative of the presence of a container during an inspection interval, and maintaining a count of the number of containers inspected based on the signal indicative of the presence of the container.

10. Method according to claims 1, 3 or 5 including the step of maintaining a count of the number of containers which should be rejected based on the reject signal.

11. Method according to claims 1, 3 or 5 including directing light from a source at a first location with respect to the container to the surface of the container and detecting light reflected from the surface of the container at a second location with respect to the container.

12. Method according to claim 11 wherein the path of light between the first location and the surface of the container and the path of light between the surface of the container and the second location intersect the plane of the surface of the container at relatively acute angles.

13. Apparatus for inspecting containers for manufacturing defects, comprising:
   means for directing a beam of light to a portion of the surface of a container during an inspection interval,
   means for causing relative angular displacement between the beam and the container,
   means for detecting light reflected from the container and for generating a time varying signal having a value based on the detected light,
   means for repetitively computing in real time the time rate of change of the signal,
   means for comparing each computed time rate of change to a preselected number,
   means for generating a reject signal indicating whether a container should be rejected based on the comparison of the computed time rate of change to the preselected number.

14. Apparatus for inspecting containers for manufacturing defects, comprising:
   means for directing a beam of light to a portion of the surface of a container during an inspection interval,
   means for causing relative angular displacement between the beam and the container,
   means for detecting light reflected from the container and for generating a time-varying signal having a value based on the detected light,
   means for repetitively sampling the signal during the inspection interval,
   means for storing a predetermined number of samples of the signal,
   means for updating the stored samples in real time,
   means for computing the difference between a first updated stored sample and a second updated stored sample which is later in time than the first stored sample,
   means for comparing the computed difference to a preselected number, and
   means for generating a reject signal indicating whether a container should be rejected based on the comparison of the computed difference to the preselected number.

15. Apparatus according to claim 14 wherein said means for repetitively sampling said signal includes means for repetitively sampling the signal at a sampling rate and sampling interval dependent on the duration of the inspection interval such that the number of samples obtained during any inspection interval is substantially constant.

16. Apparatus according to claim 14 wherein said means for storing and updating said predetermined number of samples includes means for updating the predetermined number of samples stored on a first in, first out basis.

17. Apparatus for inspecting containers for manufacturing defects, comprising:
   means for directing a beam of light to the surface of a container during an inspection interval,
   means for causing relative angular displacement between the beam and the container,
   means for detecting light reflected from a container and for generating a time-varying signal having a value based on the detected light,
   means for repetitively sampling the signal at a rate dependent on the duration of an inspection interval such that the number of samples obtained during any inspection interval is substantially constant,
   means for storing a predetermined number of samples and for updating the stored samples in real time by removing the oldest stored sample and by storing the newest sample,
   means for computing the difference between the oldest updated stored sample and the newest updated stored sample,
   means for comparing the computed difference to a preselected number, and
   means for generating a reject signal indicating whether a container should be rejected based on the comparison of the computed difference to the preselected number.

18. Apparatus according to claims 17 or 15 including means for automatically determining the duration of a preceding inspection interval, and means for automatically varying said rate and interval of repetitive sampling of the signal based on the duration of the preceding inspection interval.

19. Apparatus according to claims 14 or 17 wherein said means for repetitively sampling the signal includes a sample and hold circuit, an analog to digital converter connected to the sample and hold circuit, and means for automatically varying the rate of operation of the sample and hold circuit and the analog to digital converter based on the duration of the inspection interval.

20. Apparatus according to claim 19 wherein said means for detecting light and for generating a signal having a value based on the detected light includes a high gain inverter amplifier connected to the sample and hold circuit.

21. Apparatus according to claims 13, 14 or 17 including means for ejecting a container in response to said reject signal.

22. Apparatus according to claim 21 including means for generating a diagnostic signal, means for detecting presence or absence of said diagnostic signal, and means for inhibiting said step of ejecting said container if absence of said diagnostic signal is detected.

23. Apparatus according to claims 13, 14 or 17 including means for detecting the presence of a container during an inspection interval, and means for maintaining a count of the number of containers detected.

24. Apparatus according to claims 13, 14 or 17 including means for maintaining a count of the number of containers which should be rejected based on the reject signal.

25. Apparatus according to claims 13, 14 or 17 wherein said means for directing light includes means for directing light from a first location with respect to a container to the surface of the container and wherein said means for detecting light includes means for detecting light reflected from the surface of the container at a second location with respect to the container.

26. Apparatus according to claims 13, 14 or 17 including means for rotating a container about its longitudinal axis while light is being directed to the portion of the surface of the container.

27. Method of inspecting containers for manufacturing defects in the walls and on the inner and outer surfaces of the containers, comprising the steps of:
   (a) optically scanning a plurality of selected contiguous and substantially non-overlapping zones of a container during an inspection interval,
   (b) generating separately for each zone a signal having a time-varying value representative of the optical characteristics of the zone being scanned,
   (c) repetitively sampling each said signal during the inspection interval at a rate dependent on the duration of the inspection interval such that the number of samples obtained during any inspection interval is substantially equal to the number of samples obtained during any other inspection interval,
   (d) storing a predetermined number of samples of each said signal and repetitively updating the stored samples in real time by removing the oldest stored sample and by storing the newest sample,
   (e) computing the time rate of change of each said signal by comparing the value of the oldest updated stored sample of the signal to the value of the newest updated stored sample of the same signal subsequent in time to the oldest updated stored sample,
   (f) comparing the computed time rate of change of each said signal to a preselected number, and
   (g) generating a reject signal indicating whether the container should be rejected based on the comparison between the computed time rate of change and the preselected number.

28. Method according to claim 27, wherein said zones are substantially perpendicular to the longitudinal axis of the container.

29. Method according to claim 27, wherein the step of optically scanning includes the steps of:
   (i) directing a beam of light onto a predetermined region of the container,
   (ii) causing relative angular displacement between the beam and the container whereby the beam sweeps across a zone substantially perpendicular to the longitudinal axis of the container, and
   (iii) detecting the light reflected from the container as the beam sweeps across the zone.

30. Apparatus for inspecting containers for manufacturing defects in the walls and on the inner and outer surfaces of the containers, comprising:
   (a) means for optically scanning a plurality of selected contiguous and substantially non-overlapping zones of a container during an inspection interval,
   (b) means for generating separately for each zone a signal having a time-varying value representative of the optical characteristics of the zone being scanned,
   (c) means for repetitively sampling each said signal during the inspection interval at a rate dependent on the duration of the inspection interval, such that the number of samples obtained during any inspection interval is substantially equal to the number of samples obtained during any other inspection interval,
   (d) means for storing a predetermined number of samples of each said signal and repetitively updating the stored samples in real time by removing the oldest stored sample and storing the newest sample,
   (e) means for computing the time rate of change of each said signal by comparing the value of the oldest updated stored sample of the signal to the value of the newest updated stored sample of the same signal subsequent in time to the oldest updated stored sample,
   (f) means for comparing the computed time rate of change of each said signal to a preselected number, and
   (g) means for generating a reject signal indicating whether the container should be rejected based on the comparison between the computed time rate of change and the preselected number.

31. Apparatus according to claim 30, wherein said zones are substantially perpendicular to the longitudinal axis of the container.

32. Apparatus according to claim 30, said means for optically scanning further comprising,
   (i) means for directing a beam of light onto a predetermined region of the container,
   (ii) means for causing relative angular displacement between the beam and the container whereby the beam sweeps across a zone substantially perpendicular to the longitudinal axis of the container, and
   (iii) means for detecting the light reflected from the container as the beam sweeps across the zone.

* * * * *